(12) United States Patent
Drynkin et al.

(10) Patent No.: US 9,791,467 B2
(45) Date of Patent: Oct. 17, 2017

(54) ADJUSTABLE ROBOTIC PICKER FOR LABORATORY CONTAINERS

(71) Applicants: Alexander V. Drynkin, San Ramon, CA (US); David B. Miller, Orinda, CA (US)

(72) Inventors: Alexander V. Drynkin, San Ramon, CA (US); David B. Miller, Orinda, CA (US)

( * ) Notice: Subject to any disclaimer, the term of this patent is extended or adjusted under 35 U.S.C. 154(b) by 336 days.

(21) Appl. No.: 14/450,852

(22) Filed: Aug. 4, 2014

(65) Prior Publication Data

US 2016/0033540 A1    Feb. 4, 2016

(51) Int. Cl.
*G01N 35/00* (2006.01)
*B25J 15/10* (2006.01)
*G01N 35/10* (2006.01)

(52) U.S. Cl.
CPC .......... *G01N 35/0099* (2013.01); *B25J 15/10* (2013.01); *G01N 35/109* (2013.01); *Y10S 901/02* (2013.01)

(58) Field of Classification Search
CPC .. G01N 35/0099; G01N 35/10; G01N 35/109; B25J 15/10
See application file for complete search history.

(56) References Cited

U.S. PATENT DOCUMENTS

2013/0019697 A1\* 1/2013 McKeen ................ G01N 1/312
73/863.21

\* cited by examiner

*Primary Examiner* — Erika J Villaluna
(74) *Attorney, Agent, or Firm* — Richard Esty Peterson

(57) ABSTRACT

A robotic picker with a pick head unit for a robotic tube handler that provides for automated transport and sampling of laboratory tubes, the picker having a prong picker with a multiple of depending pick prongs optimized for an orthogonal arrangement of tubes, typically in a tube rack, wherein the pick head unit has a mechanism for shifting the radial orientation of the pick head unit to accommodate both orthogonal and diagonal arrangements of laboratory tubes.

16 Claims, 6 Drawing Sheets

ADJUSTABLE ROBOTIC PICKER FOR LABORATORY CONTAINERS

CROSS-REFERENCE TO RELATED APPLICATIONS

Not Applicable

FEDERALLY SPONSORED RESEARCH

Not Applicable

SEQUENCE LISTING OR PROGRAM

Not Applicable

FIELD OF INVENTION

This invention relates to a robotic picker for laboratory containers that has the capability of accommodating a variety of different laboratory containers, typically test tubes of different size and test tube racks having different configurations.

BACKGROUND

This invention relates to a robotic picker for laboratory containers, typically laboratory sample tubes and containers that vary in size and in the arrangement of the containers in the racks and trays that hold the containers. The term, containers, connotes typical laboratory tubes that vary in size and the term includes small diameter tubes, vials, and small dishes.

Such containers are typically arranged orthogonally in perpendicular rows or staggered in diagonal rows. Individual containers may be supported in racks or on trays and the like. The variety of sample containers has provided a challenge to the developers of robotic equipment to make mechanisms for robotic pickers that can accommodate the different sizes and arrangements of sample containers presented to the computer controlled robotic apparatus. The computer controlled robotic apparatus is employed to selectively access and displace individual containers according to programmed protocols. A particular challenge is to provide a robotic picker with a pick head that can access containers arranged both orthogonally in perpendicular rows and staggered in diagonal rows. The container arrangement staggered in diagonal rows is commonly called a honeycomb configuration.

SUMMARY OF THE INVENTION

The adjustable robotic picker of this invention relates to a robotic pick head unit that can be incorporated into a variety of automated tube handlers that access a platform of laboratory test tubes and/or containers. The pick head unit is typically transported by a transport system that includes an elevated transport structure with drive motors and a track layout that enables the pick head unit to access any one of the tubes or containers on the platform as well as any auxiliary devices or stations. The terms tube and container are used interchangeably and include common laboratory test tubes, vials, rack-contained miniature tubes, rack wells, petri dishes and even pipet tips. For convenience, the term, tube, will be used instead of the broader term, container, as the containers are typically tubular and the geometry in part dictates the number and arrangement of the pick elements that grasp, retain and release the variety of tubular containers.

In one preferred embodiment used as an example, the robotic tube handler has a pick head unit coupled to a sample extraction and inoculation mechanism that share much of the transport system. The off-set of the coupled devices is easily accommodated in the programming for moving the coupled apparatus in the X-Y directions, but selectively moving the separated units in the up-down Z direction. It is to be understood that the pick head unit in many, if not most, instances will be used in a robotic tube handler without the sample extraction and inoculation mechanism.

The pick head unit has a plurality of depending pick prongs that expand from a tight constricted position to an optimum spread, depending on the diameter of the top of the tube to be accessed. A protocol is maintained for automatically adjusting the spread of the pick prongs according to the particular tubes supported on a platform of the robotic tube handler. The protocol is maintained in the operating software of the tube handler in a manner that permits updating for new tubes of different dimensions or carried in tube racks or on tube trays in an arrangement that is different than the typical orthogonal array. The robotic tube handler typically has an internal processor and a controller to execute the software program. An auxiliary general-purpose computer is typically connected to or incorporated into the robotic tube handler for convenience in maintaining the software and protocol.

An important feature of this invention is the ability of the pick head unit to adjust for both orthogonal and "honeycomb" or diagonal racks that are commonly used for containing grouped laboratory tubes. When laboratory tubes are arranged in tightly packed groups, the spacing between the cylindrical tubes not positioned on the outer perimeter, is greatest at four positions around each tube. It is at these four positions that the prongs of the pick head unit can insert and grip the top of the tube before lifting and transporting to another location.

In the situation of the orthogonally arranged tubes, the prongs are preferably four in number and are orthogonally located. In the situation of the diagonally arranged tubes the greatest spacing is off-set by forty five degrees. It is an objective to devise a pick head unit that can be adapted to automatically switch from one position to another to accommodate laboratory tubes that are arranged either orthogonally or diagonally in a robotic tube handler.

These and other features of the invention will be apparent from a consideration of the detailed description of the preferred embodiment.

DETAILED DESCRIPTION OF THE PREFERRED EMBODIMENTS

Figure 1:
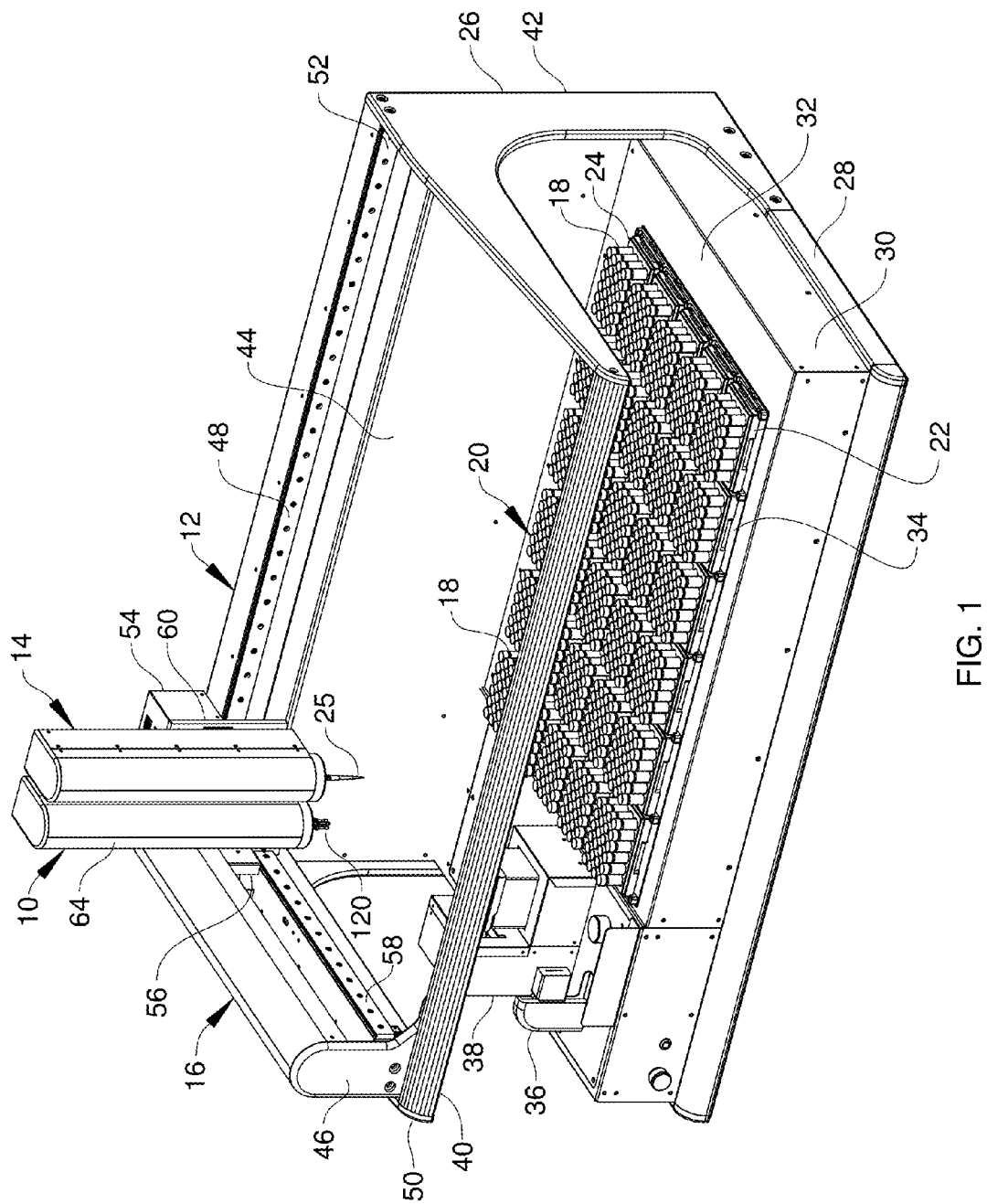
FIG. 1 is a perspective view of a robotic tube handler with the robotic picker installed to grip and transport select tubular containers, here small laboratory tubes.

Referring to FIG. 1, the robotic picker 10 is shown incorporated into a robotic tube handler 12 for automated tube transport and sampling. In a preferred embodiment the robotic picker is shown coupled to a sample extraction and inoculation mechanism 14. The sample extraction and inoculation mechanism 14 is off-set from the robotic picker 10 and utilizes the same transport system 16 as the robotic picker 10 with the software program adjustments necessary to accommodate for the off-set when addressing a particular tube 18 in a tube array 20. The tube array 20 in the example of FIG. 1 is a composite of a tube rack array 22 of thirty tube racks 24.

The software program controlling the transport system 16 directs either the robotic picker 10 or the sample extraction and inoculation mechanism 14 to a specific tube for a directed operation. Such operation for the robotic picker may include removal of a tube for weighing, cap removal, volume measurement, relocation, labeling or a variety of other operations that a particular robotic tube handler is capable of performing.

Similarly, the sample extraction and inoculation mechanism 14 may be located to a particular tube for extracting a sample, creating a sample or adding a substance to an existing sample. The sample extraction and inoculation mechanism 14 is shown with a depending pipet tip 25. In certain robotic tube handlers, the robotic picker 10 may assist in the removal and replacement of the pipet tip 25. The scope of operations and capabilities of a particular tube handler is not detailed in this disclosure and the robotic tube handler described is an example of the type of tube handler that can benefit from the robotic picker of this invention.

The tube handler 12 of FIG. 1 is an example of a relatively sophisticated robotic tube handler. The robotic tube handler 12 has a support structure 26 with a base 28, a housing 30 that contains the power system and control electronics (not shown) and a deck 32 with a platform 34 for the tube racks 24. The deck 32 also includes a tube label reader 36 and a weighing or volume measuring station 38. Other operational stations such as a tube parking station may be included, but are not shown in this example of a tube handler 12.

The support structure 26 of the robotic tube handler 12 also includes an elevated support frame 40 cantilevered from two integral support legs 42 for the transport system 16. A back wall 44 from the base 28 to the support frame 40 prevents inadvertent access to the working area of the robotic tube handler 12.

The transport system 16 includes a transport bridge 46 that rides on rails 48 on two opposite sides of the support frame 40. The transport bridge 46 is shown at one end 50 of the support frame 40, and can be directed toward the opposite end 52 by a first horizontal drive motor assembly 54 at one end of the transport bridge 46. A similar drive motor assembly 56 displaces the co-joined robotic picker 10 of this invention with the sample extraction and inoculation mechanism 14 on a bridge track 58. A third drive motor assembly 60 raises and lowers the robotic picker 10 and the sample extraction and inoculation mechanism 14 in tandem or separately depending on the capabilities of the tube handler 12. The features of the tube handler are described in general to assist in understanding the subject robotic picker 10, which is the focus of this description.

Figure 2:
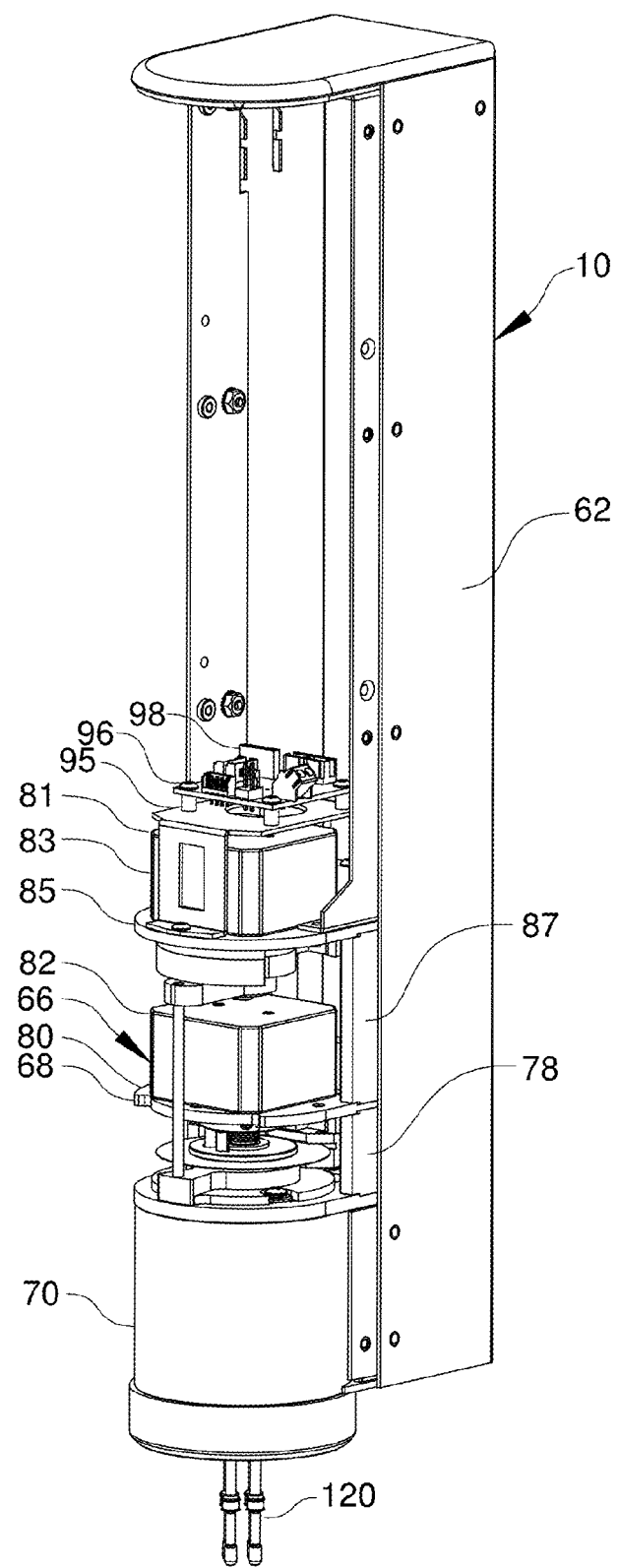
FIG. 2 is a perspective view of the robotic picker of FIG. 1 with a vertical cover removed to reveal the pick head unit.
Figure 3:
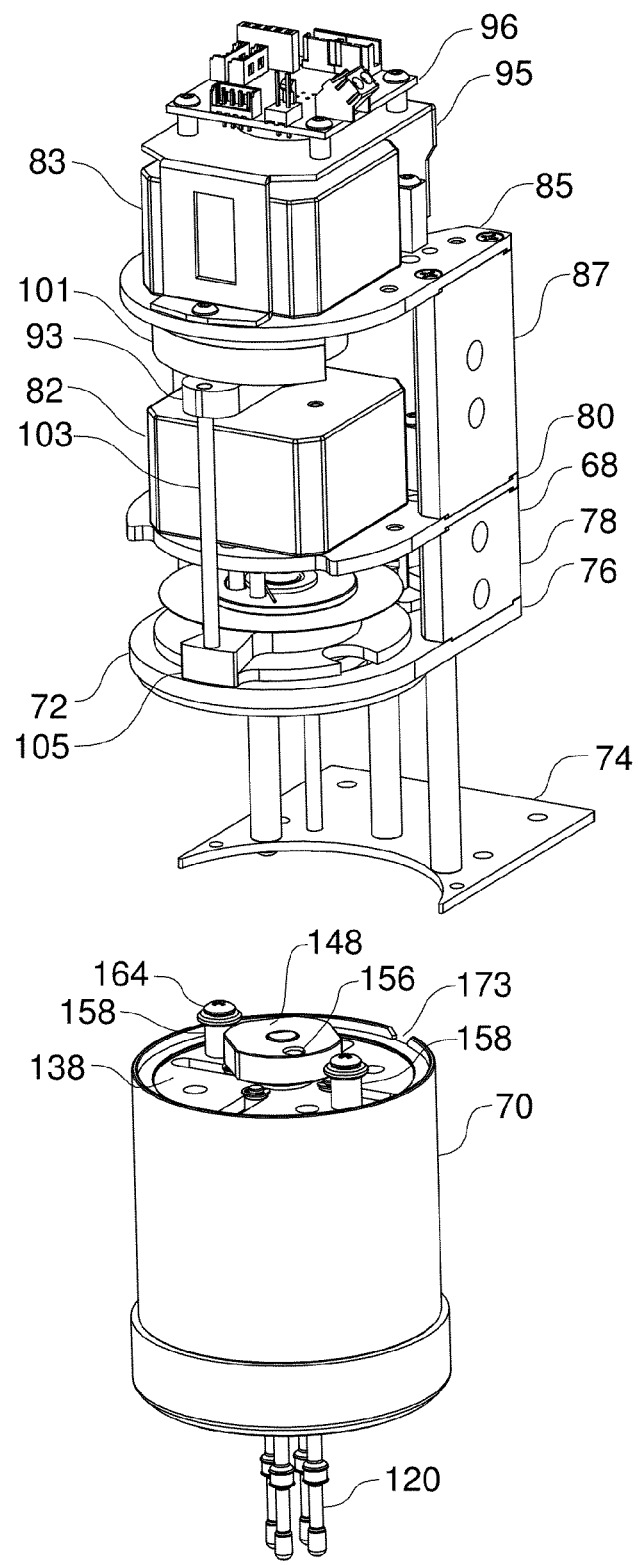
FIG. 3 is a partially exploded view of the pick head unit of FIG. 2 showing the drive assembly separated from the pick actuator assembly.

Referring to FIG. 2, the robotic picker 10 has an elongated housing 62 with the vertical cover 64 shown in FIG. 1 removed. The robotic picker 10 has an electronically operated pick head unit 66 with a drive motor assembly 68 coupled to a pick actuator assembly 70. An exploded view of the assembled drive motor assembly 68 separated from the assembled pick actuator assembly 70 is shown in FIG. 3. An exploded view of the drive assembly 68 is shown in FIG. 4 and an exploded view of the pick actuator assembly 70 is shown in FIG. 5.

As shown in FIGS. 2 and 3, a guide bracket 72 in the drive assembly 68 supports and interconnects the pick actuator assembly 70 with the drive assembly 68 and provides the mounting plates 74 and 76 for connecting the two assemblies 68 and 70 to the housing 62. Support blocks 78 displace the mounting plate 76 from a support plate 80 for a drive motor stack 81 with a prong spread motor 82 and an actuator assembly shift motor 83. The actuator assembly shift motor 83 is seated on an upper support plate 85 separated from the support plate 80 by support blocks 87.

Figure 4:
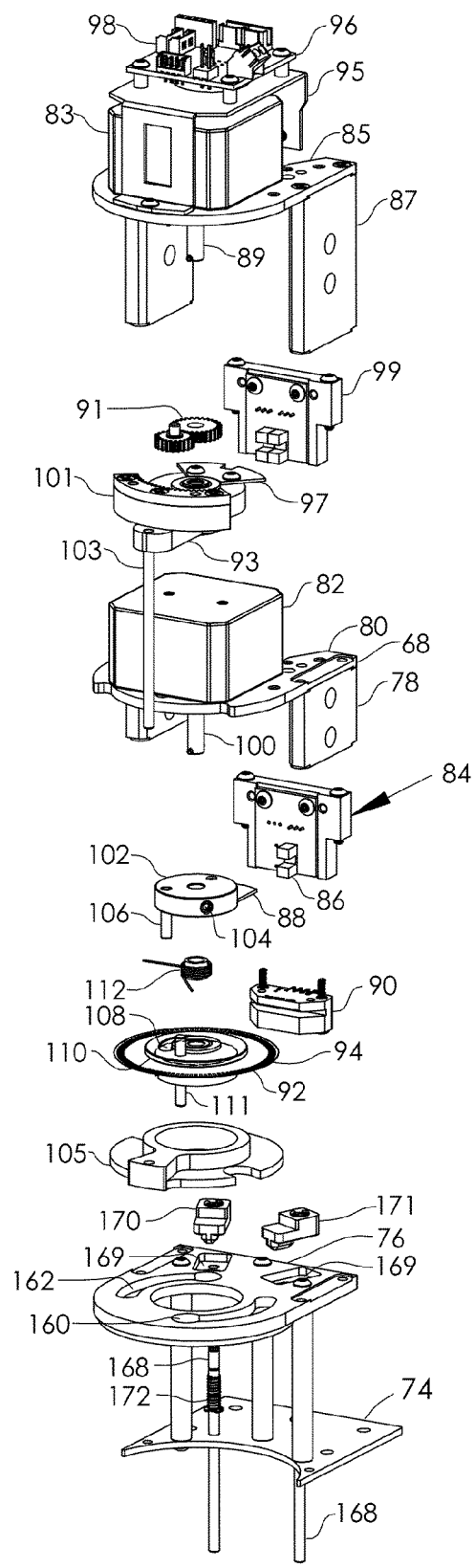
FIG. 4 is an exploded view of the pick drive assembly.
Figure 5:
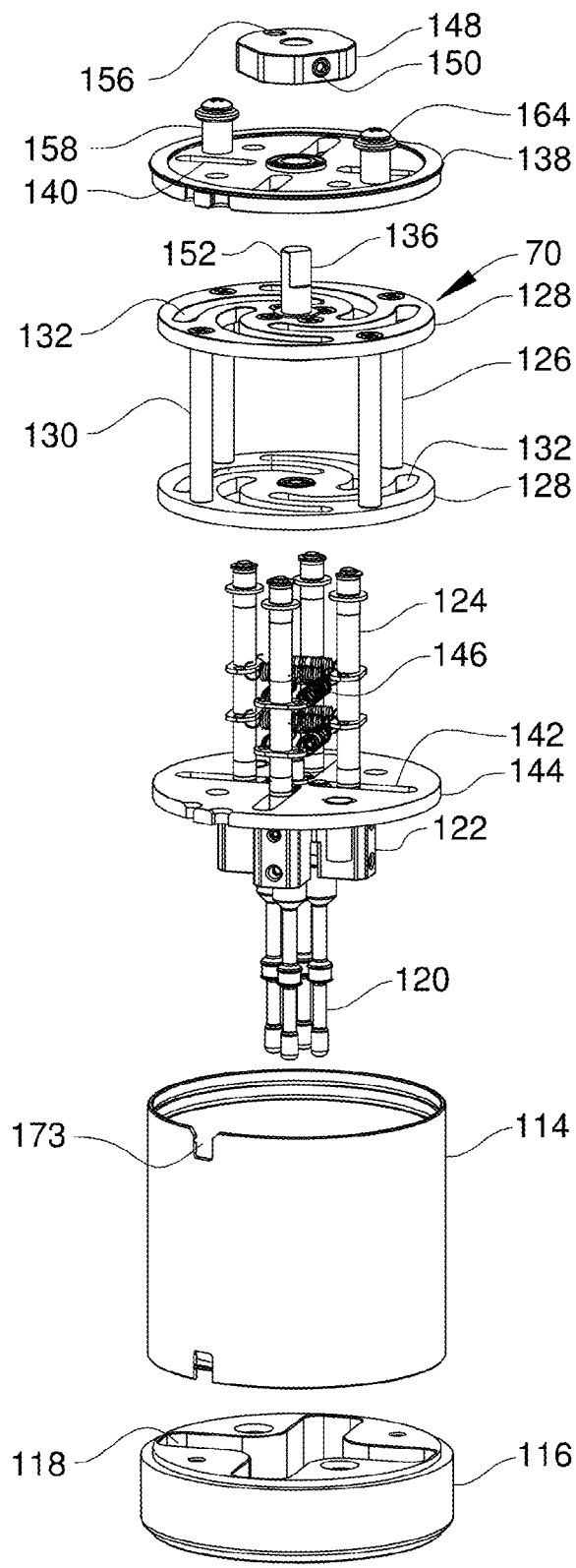
FIG. 5 is an exploded view of the pick actuator assembly.

As further revealed in the exploded view of FIG. 4 the displacement of the lower motor support plate 80 from the mounting plate 76 allows space for locating a position sensor 84 with a limit detector 86 that cooperates with a radial flag 88 to detect the start or home position of the pick actuator assembly 70 for the respective orthogonal or diagonal arrangement of tubes in a tube rack. The spacing also provides for a radial location sensor 90 that cooperates with a marked disk 92. The markings 94 in the perimeter of the disk 92 provide a count for the prong spread motor 82, which is preferably a stepping motor for a precision count from a home location. This count translates to the degree of separation of the pick elements to accommodate a particular diameter tube.

The drive motor stack 81 includes a top bracket structure 95 with an elevated electronic component board 96 having assorted connectors and terminals 98 to connect the robotic picker 10 to the operating electronics of the tube handler 12 in commanding the operation of the picker 10. It is to be understood that the robotic tube handler 12 includes a controller with an internal processor and may include an external or auxiliary processor in the form of a general-purpose computer or tablet (not shown) that can also functions as a user input and display.

The output shaft 100 of the prong spread motor 82 connects to the center of a drive collet 102 carrying the projecting radial sensor flag 88 and is secured by a set screw 104. The drive collet 102 has a depending cam pin 106 that engages an arcuate slot 108 in a guide plate 110 that is coupled to the marked sensor disk 92. The arcuate slot 108 is approximately one quarter of a radial turn and provides for installation of the pick actuator assembly 70 and for the forty five degree shift in the radial orientation of the pick actuator assembly 70 when adjusting for orthogonal or diagonal arrangements of the tubes in the tube racks being accessed.

An elongated drive pin 111 is retained by the guide plate 110 and extends downward to engage the pick actuator assembly 70 when the drive assembly 68 and actuator assembly 70 are coupled for operation. The projecting end of the output shaft 100 of the drive motor terminates in the center of the guide plate 110 and provides a support shaft for a torsion spring 112. The torsion spring 112 insures that the depending cam pin 106 is continually biased to one end of the arcuate slot 108 when the pick actuator assembly is adjusted, thereby flagging the selected start position for actuation of the pick actuator assembly 70.

The actuator shift motor 83 is also preferably a stepping motor. It has an output shaft 89 that is coupled to a reduction drive gear train 91 for an arm crank 93 that carries a slotted sensor flag 97 that cooperates with a doubled electronic stationary sensor 99 for accurately detecting the angular position of the pick actuator assembly 70. The arm crank 93 also carries an arcuate spacer and stop 101 that shelters the gear train 91 and sensor flag 97. The arm crank 93 has a drive post 103 that by-passes the drive motor assembly 68 and terminates in a driven connector plate 105 coupled to the top of the partially rotatable pick actuator assembly 70. Activation of the actuator shift motor 83 rotates the actuator assembly and contained picker mechanisms within the desired range, for example, the forty-five degree range to accommodate the orthogonal and diagonal arrangement of rack tubes.

The pick actuator assembly 70 of the robotic picker 10 is shown in the exploded view of FIG. 5. The pick actuator assembly 70 has a cylindrical casing 114 with a bottom end cap 116 having a cross-shaped opening 118. Four pick prongs 120 of the pick head unit 66 in the preferred embodiment project from the bottom end cap 116 through the cross-shaped opening with adequate room to splay. The opening 118 can be altered for differently configured prongs for grasping wide containers or different numbers of prongs for specialty grasping.

The four pick prongs 120 of the preferred embodiment are seated in socket clamps 122 at the ends of four corresponding actuator pins 124 in a cam cage 126. The cam cage 126 has two cam disks 128 spaced apart by four spacer posts 130. The two cam disks 128 have identical cam slots 132 that spiral outwardly and selectively engage the actuator pins 124 and aid in maintaining the vertical integrity of the pins 124 and hence the pick prongs 120 when spreading the actuator pins 124 apart when the cam cage 126 is rotated in a clockwise direction.

Rotation is accomplished by a drive shaft 136 fixed to the top of the upper cam disk 128. The drive shaft 136 passes through a top cap 138 having four guide slots 140 in a cross shape that match the four guide slots 142 in a support plate 144 above the socket clamps 122 that seats on the bottom end cap 116. When located in the cam cage 126, the actuator pins are biased by two sets of two springs 146 to the constricted or gripping position. A bias to the gripping position insures that a laboratory tube in the grips of the actuator pins is not dropped in the event of an electrical failure. To splay the pins apart a distance to encompass a container, the drive shaft 136 must be partially rotated wherein the outwardly directed cam slots 132 force the pins 124 to separate against the bias of the springs 146. The degree of separation is determined by the step count of the drive motor 82 as determined by the sensor disk 92 in accordance with the protocol for the size of tubes being handled.

The drive shaft 136 is attached to a disk-like collet 148 by contact of a setscrew 150 on a shaft flat 152. The collet 148 has a center axis of rotation and an off-center hole socket 156 displaced from the center axis that is engaged by the elongated, depending drive pin 111 of the drive assembly 68. On rotation of the drive collet 102, the off-set drive pin 111 interconnecting the drive collet 102 with the driven collet 148 acts as a crank and rotates the driven collet 148 on its axis together with the connected cam cage 126, and as a consequence, spreads or splays the four pick prongs 120 according to the programmed protocol for a particular tube or cap diameter.

Referring again to FIG. 3, the pick actuator assembly 70 is suspended from the mounting plate 76 by two opposed bosses 158 projecting from the top cap 138. The two bosses 158 insert up through enlarged openings 160 in two opposed arcuate guide slots 162 and are retained in a slidable suspension by the screw and washer assembly 164 on the top of each boss 158. This arrangement allows the pick actuator assembly 70 to be grasped, lifted up into the guide opening after engaging the drive pin 111 and rotating the bosses into the arcuate guide slots 162. The screw and washer assembly 164 has a spring load to enable the rotation of the pick actuator assembly 70 when shifting positions. The pick actuator assembly 70 is thereby removable and installable manually and rotatable within limits.

Radial stops for the limited rotation to one of two positions at the ends of the forty five degree displacement for accommodating the two tube arrangements is accomplished by two spring-loaded, detent actuator pins 168. The detent actuator pins 168 pass up through the mounting plate 76 and through the lower mounting plate 74 and engage two detents 170 and 171. The detents 170 and 171 are seated in recesses 169 in the mounting plate 76 and have a depending part that extends through an opening in each recess 169.

Springs 172 (one visible in FIG. 4) seated proximate the ends of the detent actuator pins 168 are compressed against the underside of the mounting plate 76 and urge the detents 170 and 171 downwardly to allow selective engagement of one of the detents with a cam notch 173 in the top lip of the cylindrical casing 114 of the pick actuator assembly 70. To retract a detent 170 or 171 that has engaged the notch 173, the actuator shift motor 83 is activated and the detents 170 or 171 act as cam followers and rise from the cam notch 173. The connected pins 168, which projects a short distance from the lower mounting plate 74, can be pressed by a user's finger to lift the engaged part of the detent from the notch 173 when removing the pick actuator assembly 70. In this manner each of the two alternate positions can be easily detected by the relative position of the projectable pins 168 and the pick actuator assembly 70 can be changed manually or the assembly 70 can be removed with the power off.

Figure 6A:
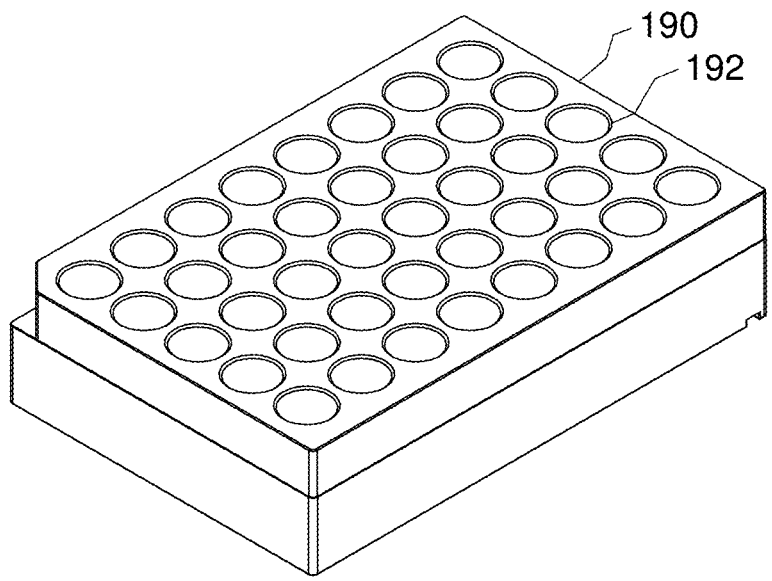
FIG. 6A is a perspective view of a typical orthogonally arranged tube rack for laboratory tubes.

A typical rack 190 with an orthogonal arrangement of receptacles 192 for laboratory tubes is shown in FIG. 6A.

Figure 6B:
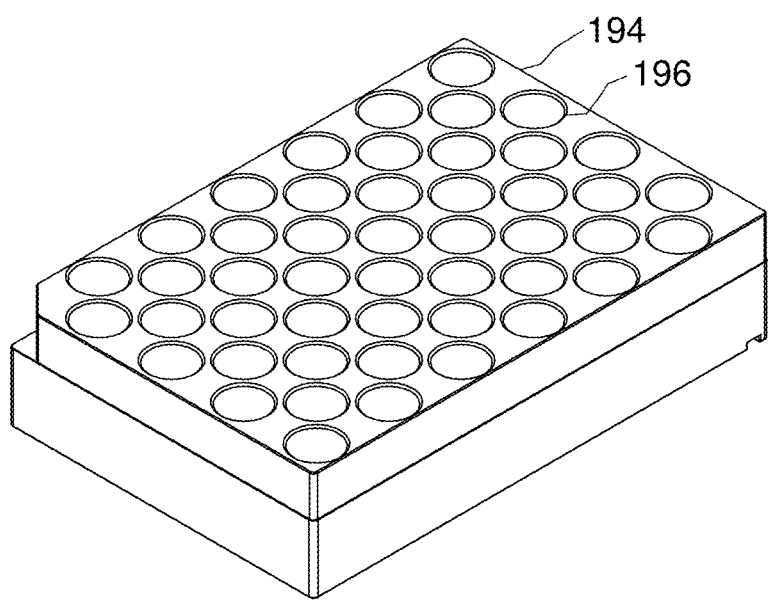
FIG. 6B is a perspective view of a typical diagonal or "honeycomb" rack for the alternate arrangement of laboratory tubes.

A typical rack 194 with a diagonal arrangement, also called a "honeycomb" arrangement, of receptacles 196 for laboratory tubes is shown in FIG. 6B.

It is to be understood that once the pick actuator assembly 70 is installed on the drive assembly it can be actuated automatically with the actuator shift motor 83.

It is also to be understood that the clamp-seated pick prongs can be modified internally at the clamp, or externally at the cushion bulge to accommodate prongs that have a range as extended to encompass dishes, as in an array of small petri dishes on a tray, or a reduced number of prongs, such as two opposed prongs with arcuate gripping surfaces.

While the preferred embodiment has been described with some particularity, it is to be understood that modifications can be made without departing from the spirit of the invention and the scope of the claims.

The invention claimed is:

1. In a robotic tube handler for automated tube transport and sampling of tubes, the tube handler having a transport system that transports tubes and an electronic control system that robotically controls the transport system, a robotic picker operationally connected to the robotic tube handler, the robotic picker comprising:
- a pick head unit with a housing that houses the pick head unit, the pick head unit including four depending pick prongs, the pick head unit having a drive motor assembly and a pick actuator assembly wherein the pick head unit is mechanically coupled to the transport system and the pick head unit is electronically coupled to the control system, wherein,
- the drive motor assembly has a first drive motor and controller electronics to drive the first drive motor according to commands from the control system of the tube handler, and a second drive motor and controller electronics to drive the second drive motor according to commands from the control system of the tube handler, and
- the pick actuator assembly is coupled to the first drive motor assembly with a selectable rotational displacement with respect to the first drive motor assembly to automatically accommodate various arrangements of tubes, including both orthogonal and diagonal arrangements of tubes, when the first drive motor is activated in the robotic picker under control of the robotic tube handler control system, and, wherein,
- the pick actuator assembly has detent stops limiting the rotation of the drive motor assembly and on activation of the first drive motor the pick actuator assembly is rotated forty-five degrees in rotational displacement, and
- the pick actuator assembly has cam mechanics connected to the depending pick prongs and to the second drive motor that spread the depending pick prongs on activation of the second drive motor.

2. The robotic picker in the robotic tube handler of claim 1 wherein the pick actuator assembly is releaseably coupled to the drive motor assembly and removeable by human hand rotation.

3. The robotic picker in the robotic tube handler of claim 1 wherein the second drive motor has an output shaft, a crank drive element with a center axis with a depending drive pin displaced from the center axis of the crank drive element, the output shaft being connected to the crank drive element at the center axis, and a crank driven element that is center mounted on the pick actuator assembly the crank driven element having a center axis, wherein the drive pin is connected to the center mounted crank driven element on the pick actuator assembly, and wherein the drive pin is connected to the crank driven element displaced from the center axis of the crank driven element.

4. The robotic picker in the robotic tube handler of claim 1 wherein the pick actuator assembly has a cylindrical casing with a top lip having a cam notch, and the detent stops include a pair of spring-loaded detents mounted in the drive motor assembly that selectively engage the cam notch.

5. The robotic picker in the robotic tube handler of claim 1 wherein the drive motor assembly has an upper motor support plate on which the first drive motor is mounted and a lower motor support plate under the upper motor support plate on which the second drive motor is mounted.

6. The robotic picker in the robotic tube handler of claim 1 wherein the drive motor assembly has a position sensor and a marked disk for determining the radial displacement of an output shaft of the second drive motor.

7. The robotic picker in the robotic tube handler of claim 6 wherein the drive motor assembly has a limit detector and a flag for determining the radial orientation of the pick actuator assembly relative to the drive motor assembly.

8. The robotic picker in the robotic tube handler of claim 1 wherein the pick actuator assembly has a top cap with two projecting bosses each with a retainer assembly, and the drive motor assembly has a bottom mounting plate with two opposed arcuate guide slots, wherein the projecting bosses are insertable up into the guide slots and retained by the retainer assembly for limited rotation of the pick actuator assembly relative to the drive motor assembly by the insertable bosses in the guide slots.

9. The robotic picker in the robotic tube handler of claim 1 wherein the pick actuator assembly has a cam cage with spaced apart cam disks with four identical cam slots that spiral outwardly and with four actuator pins engaged in the cam slots, the actuator pins having upper and lower ends, the lower ends being connected to the four depending pick prongs, wherein the cam cage is connected to the second drive motor for rotation of the cam cage relative to the drive motor assembly to spread the pick prongs.

10. The robotic picker in the robotic tube handler of claim 9 wherein a top cap of the pick actuator assembly has four guide slots in a cross shape wherein the upper ends of the actuator pins are guided and retained by the top cap and displaceable in the guide slots on rotation of the cam cage.

11. The robotic picker in the robotic tube handler of claim 1 wherein the first drive motor of the drive motor assembly has an output shaft that is connected to a drive crank having a central axis and a depending drive post displaced from the central axis that connects to a driven crank located under the second drive motor and connected to the pick actuator assembly wherein on activation of the first drive motor and rotation of the output shaft, the pick actuator assembly is rotated within limits.

12. The robotic picker in the robotic tube handler of claim 11 wherein the output shaft of the one drive motor is first connected to a reduction gear train before the connection to the drive crank that is connected by the drive post to the driven crank.

13. The robotic picker in the robotic tube handler of claim 12 wherein the drive crank connected to the first drive motor has a sensor flag that cooperates with a stationary sensor to determine the positioning of the drive motor assembly relative to the pick actuator assembly.

14. The robotic picker in the robotic tube handler of claim 1 wherein the first drive motor has a support plate on which the first drive motor is mounted and the support plate has a support bracket for supporting the controller electronics.

15. The robotic picker in the robotic tube handler of claim 1 wherein the depending pick prongs are replaceable allowing substitute pick prongs to accommodate a greater range of tubes.

16. The robotic picker in the robotic tube handler of claim 1 in combination with a robotic tube handler.

* * * * *